(12) United States Patent
Bergmann et al.

(10) Patent No.: US 7,358,058 B2
(45) Date of Patent: Apr. 15, 2008

(54) METHOD AND AGENTS FOR THE DIAGNOSIS AND THERAPY OF CHRONIC INFLAMMATORY INTESTINAL DISEASE

(75) Inventors: Andreas Bergmann, Berlin (DE); Marita Willnich, Berlin (DE); Detlef Schuppan, Bubenreuth (DE)

(73) Assignee: B.R.A.H.M.S Aktiengesellschaft, Henningsdorf (DE)

( * ) Notice: Subject to any disclaimer, the term of this patent is extended or adjusted under 35 U.S.C. 154(b) by 146 days.

(21) Appl. No.: 10/490,597

(22) PCT Filed: Sep. 3, 2002

(86) PCT No.: PCT/EP02/09848

§ 371 (c)(1),
(2), (4) Date: Oct. 21, 2004

(87) PCT Pub. No.: WO03/029824

PCT Pub. Date: Apr. 10, 2003

(65) Prior Publication Data

US 2005/0074818 A1    Apr. 7, 2005

(30) Foreign Application Priority Data

Sep. 28, 2001   (DE)   ................. 101 47 991

(51) Int. Cl.
G01N 33/53   (2006.01)
G01N 33/567   (2006.01)
G01N 33/564   (2006.01)
G01N 33/563   (2006.01)
A61K 38/17   (2006.01)

(52) U.S. Cl. .................. 435/7.2; 435/4; 435/7.1; 436/506; 436/507; 436/512; 436/513

(58) Field of Classification Search .................. None
See application file for complete search history.

(56) References Cited

U.S. PATENT DOCUMENTS

| | | | | |
|---|---|---|---|---|
| 4,865,970 | A | * | 9/1989 | Brot et al. .................. 435/7.95 |
| 5,637,454 | A | * | 6/1997 | Harley ............................ 435/5 |
| 5,691,151 | A | * | 11/1997 | Braun et al. .................. 435/7.2 |
| 6,897,287 | B1 | * | 5/2005 | Harley ........................ 530/327 |

OTHER PUBLICATIONS

Barnard et al., Cancer Res Jun. 1, 1992; 52:3067-3072.*
Anti-Ribosomal P Elisa assay from IMMCO diagnostics, Inc., see product detail sheet, printed Jul. 31, 2001.*
Uechi et al., Genomics 2001; 72:223-230.*
Perkal et al., Gastroenterol Clin North Am. Sep. 1989;18(3):567-78, Abstract only.*
Homberg et al., Clin Exp Immunol 1974; 17,617-628.*
Nieradko-Iwanicka et al., Pol Arch Med Wewn. Jun. 2006;115(6):559-64, abstract only.*
Koutroubakis et al., Eur J Gastroenterol Hepatol. May 1998;10(5):437-9, abstract only.*
Stevens et al., Br J Dermatol. Mar. 1994;130(3):385-9, abstract only.*
Lahita, Ed. Systemic Lupus Erythematosus. Third Edition. Academic Press. San Diego. 1999, pp. 739 and 744.*
Roozendaal, C. et al. "Are anti-neutrophil cytoplasmic antibodies (ANCA) clinically useful in inflammatory bowel disease (IBD)?" Clin Exp Immunol (1999) 116:206-213.
J.-C. Homberg et al. "Ribosomal Antibodies Detected by Immunofluorescence in Systemic Erythematosus and other Collagenosis," Clin. exp. Immunol. (1974) 17:617-628.
J.B. Winfield "Are anti-ribosomal P protein antibodies a type of anti-lymphocyte antibody?" Clin. Exp. Immunol. (1997) 109:1-3.
Stafford HA et al. "Anti-ribosomal and 'P-peptide'-specific autoantibodies bind to T lymphocytes," Clin. Exp. Immunol. (1997) 109:12-19.
H.-H. Sun et al. "The expression of acidic ribosomal phosphoproteins on the surface membrane of different tissues in autoimmune and normal mice which are the target molecules for anti-double-stranded DNA antibodies," Immunology (1996) 87:362-371.
David T. Grabowski et al. "Drosophila AP3, a presumptive DNA repair protein, is homologous to human ribosomal associated protein P0," Nucleic Acids Research, vol. 19, (1991) 4297.
Nobuo Kondoh et al. "Identification and Characterization of Genes Associated with Human Hepatocellular Carcinogenesis," Cancer Res. (1999) 59: 4990-4996.
M.A. Rodrigues-Gabriel et al. "Phosphorylation of Ribosomal Protein P0 Is Not Essential for Ribosome Function but Can Affect Translation," Biochemistry (1998) 37:16620-16626.
G.F. Barnard et al."Increased Expression of Human Ribosomal Phosphoprotein P0 Messenger RNA in Hepatocellular Carcinoma and Colon Carcinoma," Cancer Res. (1992) 52:3067-3072.
K.-H. Sun et al. "Anti-dsDNA antibodies cross-react with ribosomal P proteins expressed on the surface of glomerular mesangial cells to exert a cytostatic effect," Immunology (1995) 85:262-269.

(Continued)

*Primary Examiner*—Manjunath Rao
*Assistant Examiner*—Cherie M Woodward
(74) *Attorney, Agent, or Firm*—Heslin Rothenberg Farley & Mesiti P.C.

(57) ABSTRACT

Methods for diagnosis, early diagnosis, differential diagnosis, assessment of the severity and therapy-accompanying monitoring and prognosis of chronically inflammatory intestinal diseases (Crohn's disease, *Colitis ulcerosa*), in which the presence and/or the amount of one or more antibodies which bind to ribosomal proteins, in particular P0 and L5, are determined in the serum, plasma, tissue samples and/or stool of a patient who is suffering from a chronically inflammatory intestinal disease or in whom such a disease is suspected. The blocking or removal of such antibodies and/or the influencing of antigen-presenting cells or specifically reactive T-cells which react to ribosomal proteins, such as P0 and L5, by suitable agents can be therapeutically utilized.

5 Claims, 4 Drawing Sheets

OTHER PUBLICATIONS

I. Ferrari et al. "Molecular Mimicry between the Immunodominant Ribosomal Protein P0 of *Trypanosoma cruzi* and a Functional Epitope on the Human $\beta_1$-Adrenergic Receptor," J. Exp. Med., vol. 182 (1995) 59-65.

S. Chatterjee et al. "Characterization of domains of the phosphoriboprotein P0 of *Plasmodium falciparum*," Mol. Biochem. Parasitol. (2000) 107:143-154.

S. Chatterjee et al. "Antibodies against Ribosomal Phosphoprotein P0 of *Plasmodium falciparum* Protect Mice against Challenge with *Plasmodium yoelli*," Infect. Immun. vol. (2000) 68:4312-4318.

A. Goswami et al. "Characterization of P0, a Ribosomal Phosphoprotein of *Plasmodium falciparum*," J. Biol. Chem. (1997) 272:12138-12143.

N. Fabien et al. "Autoantibodies Directed Against the Ribosomal P Proteins are not only Directed Against a Common Epitope of the P0, P1 and P2 Proteins," J. Autoimmun. (1999) 13:103-110.

B. Liliensiek et al. "Identification of Four Genes in Endothelial Cells Whose Expression is Affected by Tumor Cells and Host Immune Status—A Study in Ex Vivo-Isolated Endothelial Cells," Blood 92:9 (1998) 3394-3404.

R. Szyszka et al. "Kinase, a new enzyme phosphorylating the acidic P proteins from *Sacharomyces cerevisiae*," Biochim. Biophys. Acta (1996) 1293:213-221.

O. Rosorius et al. "Human Ribosomal Protein L5 Contains Defined Nuclear Localization and Export Signals," J. Biol. Chem. (2000) 275:12061-12068.

K. Hirano et al. "Interaction of the Ribosomal Protein, L5, with Protein Phosphatase Type 1," J. Biol. Chem. (1995) 270:19786-19790.

W.M. Michael et al. "Distinct Domains in Ribosomal Protein L5 Mediate 5 S rRNA Binding and Nuclear Localization," J. Biol. Chem. (1996) 271:11571-11574.

M. Claußen et al. "Functional Modules in Ribosomal Protein L5 for Ribonucleoprotein Complex Formation and Nucelocytoplasmic Transport," J. Biol. Chem. (1999) 274:33951-33958.

A Giualis et al., "Anti-5S RNA/protien (RNP) antibody levels correlate with disease activity in a patient with systemic lupus erythrematosus (SLE) nephritis," Clin. Exp. Immunol. (1994) 95:385-389.

V. Marechal et al. "The Ribosomal L5 Protein Is Associated with mdm-2 and mdm-2-p53 Complexes," Mol. Cell. Biol. (1994) 14:7414-7420.

O. Spirina et al. "Heart-specific splice-variant of a human mitochondrial ribosomal protein (mRNA processing; tissue specific splicing)," Gene (2000) 261:229-234.

J.-M. Kim et al. "Interaction of the $\beta$ Subunit of Casein Kinase II with the Ribosomal Protein L5," BBRC (1996) 226:180-186.

J.-M. Frigerio et al. "Cloning, sequencing and expression of the L5, L21, L27a, L28, S5, S9, S10 and S29 human ribosomal protein mRNAs," Biochim. Biophys. Acta (1995) 1262:64-68.

B. Gueraa et al. "p53 and the ribosomal protein L5 participate in high molecular mass complex formation with protein kinase CK2 in murine teratocarcinoma cell line F9 after serum stimulation and cisplatin tratment," FEBS Letters (1998) 434:115-120.

* cited by examiner

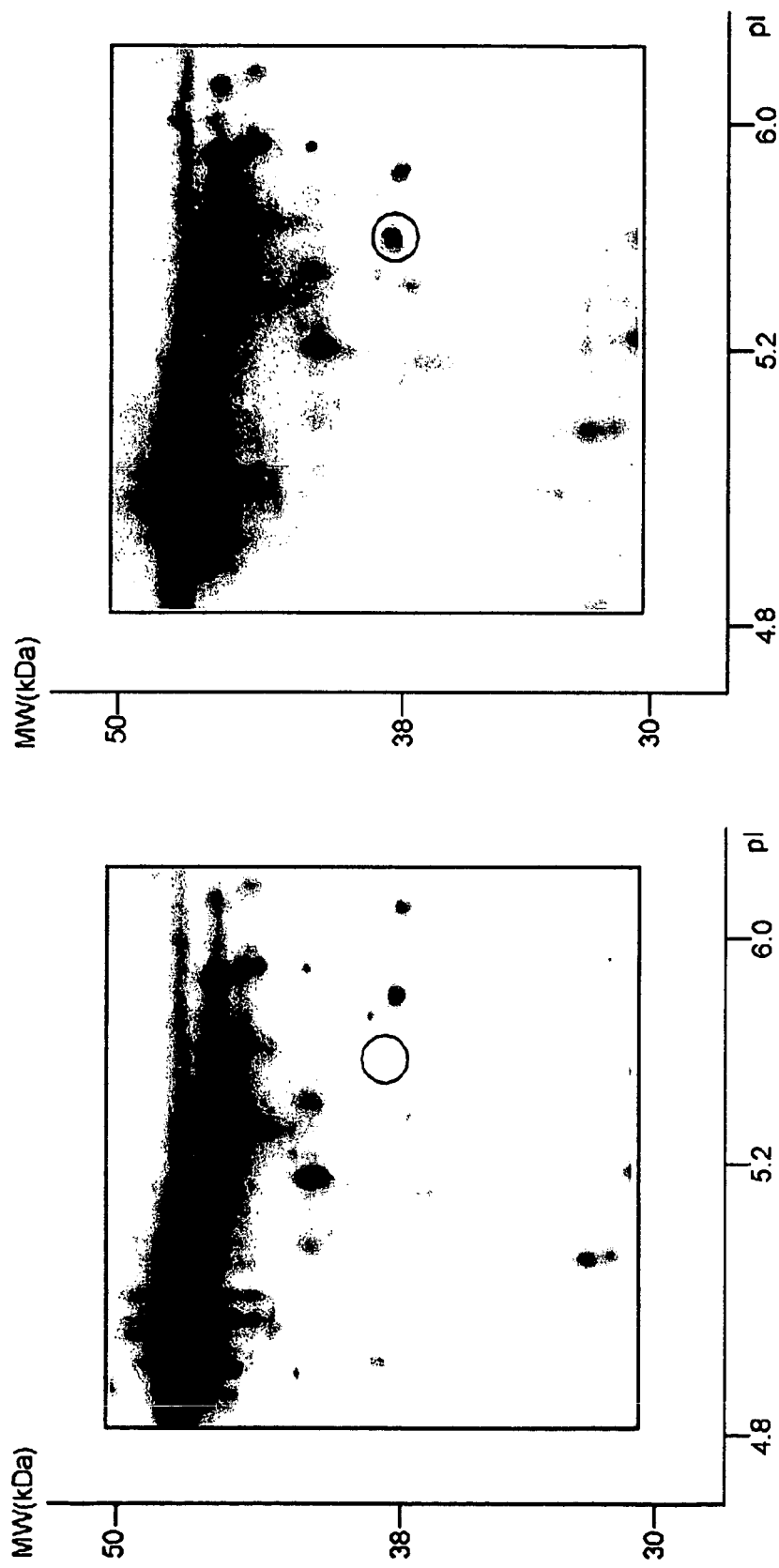

SEQUENCE LISTING

```
<160> NUMBER OF SEQ ID NOS: 2

<210> SEQ ID NO 1
<211> LENGTH: 296
<212> TYPE: PRT
<213> ORGANISM: Homo sapiens

<400> SEQUENCE: 1

Gly Phe Val Lys Val Val Lys Asn Lys Ala Tyr Phe Lys Arg Tyr Gln
  1               5                  10                  15

Val Lys Phe Arg Arg Arg Arg Glu Gly Lys Thr Asp Tyr Tyr Ala Arg
                 20                  25                  30

Lys Arg Leu Val Ile Gln Asp Lys Asn Lys Tyr Asn Thr Pro Lys Tyr
             35                  40                  45

Arg Met Ile Val Arg Val Thr Asn Arg Asp Ile Ile Cys Gln Ile Ala
         50                  55                  60

Tyr Ala Arg Ile Glu Gly Asp Met Ile Val Cys Ala Arg Tyr Ala His
 65                  70                  75                  80

Glu Leu Pro Lys Tyr Gly Val Lys Val Gly Leu Thr Asn Tyr Ala Ala
                 85                  90                  95

Ala Tyr Cys Thr Gly Leu Leu Leu Ala Arg Arg Leu Leu Asn Arg Phe
            100                 105                 110

Gly Met Asp Lys Ile Tyr Glu Gly Gln Val Glu Val Thr Gly Asp Glu
            115                 120                 125

Tyr Asn Val Glu Ser Ile Asp Gly Gln Pro Gly Ala Phe Thr Cys Tyr
        130                 135                 140

Leu Asp Ala Gly Leu Ala Arg Thr Thr Thr Gly Asn Lys Val Phe Gly
145                 150                 155                 160

Ala Leu Lys Gly Ala Val Asp Gly Gly Leu Ser Ile Pro His Ser Thr
                165                 170                 175

Lys Arg Phe Pro Gly Tyr Asp Ser Glu Ser Lys Glu Phe Asn Ala Glu
            180                 185                 190

Val His Arg Lys His Ile Met Gly Gln Asn Val Ala Asp Tyr Met Arg
        195                 200                 205

Tyr Leu Met Glu Glu Asp Glu Asp Ala Tyr Lys Lys Gln Phe Ser Gln
    210                 215                 220

Tyr Ile Lys Asn Ser Val Thr Pro Asp Met Met Glu Glu Met Tyr Lys
225                 230                 235                 240

Lys Ala His Ala Ala Ile Arg Glu Asn Pro Val Tyr Glu Lys Lys Pro
                245                 250                 255

Lys Lys Glu Val Lys Lys Lys Arg Trp Asn Arg Pro Lys Met Ser Leu
            260                 265                 270

Ala Gln Lys Lys Asp Arg Val Ala Gln Lys Lys Ala Ser Phe Leu Arg
        275                 280                 285

Ala Gln Glu Arg Ala Ala Glu Ser
    290                 295
```

```
<210> SEQ ID NO 2
<211> LENGTH: 317
<212> TYPE: PRT
<213> ORGANISM: Homo sapiens

<400> SEQUENCE: 2

Met Pro Arg Glu Asp Arg Ala Thr Trp Lys Ser Asn Tyr Phe Leu Lys
  1               5                  10                  15

Ile Ile Gln Leu Leu Asp Asp Tyr Pro Lys Cys Phe Ile Val Gly Ala
                 20                  25                  30

Asp Asn Val Gly Ser Lys Gln Met Gln Gln Ile Arg Met Ser Leu Arg
             35                  40                  45

Gly Lys Ala Val Val Leu Met Gly Lys Asn Thr Met Met Arg Lys Ala
         50                  55                  60

Ile Arg Gly His Leu Glu Asn Asn Pro Ala Leu Glu Lys Leu Leu Pro
 65                  70                  75                  80

His Ile Arg Gly Asn Val Gly Phe Val Phe Thr Lys Glu Asp Leu Thr
                 85                  90                  95

Glu Ile Arg Asp Met Leu Leu Ala Asn Lys Val Pro Ala Ala Ala Arg
                100                 105                 110

Ala Gly Ala Ile Ala Pro Cys Glu Val Thr Val Pro Ala Gln Asn Thr
            115                 120                 125

Gly Leu Gly Pro Glu Lys Thr Ser Phe Phe Gln Ala Leu Gly Ile Thr
        130                 135                 140

Thr Lys Ile Ser Arg Gly Thr Ile Glu Ile Leu Ser Asp Val Gln Leu
145                 150                 155                 160

Ile Lys Thr Gly Asp Lys Val Gly Ala Ser Glu Ala Thr Leu Leu Asn
                165                 170                 175

Met Leu Asn Ile Ser Pro Phe Ser Phe Gly Leu Val Ile Gln Gln Val
                180                 185                 190

Phe Asp Asn Gly Ser Ile Tyr Asn Pro Glu Val Leu Asp Ile Thr Glu
            195                 200                 205

Glu Thr Leu His Ser Arg Phe Leu Glu Gly Val Arg Asn Val Ala Ser
        210                 215                 220

Val Cys Leu Gln Ile Gly Tyr Pro Thr Val Ala Ser Val Pro His Ser
225                 230                 235                 240

Ile Ile Asn Gly Tyr Lys Arg Val Leu Ala Leu Ser Val Glu Thr Asp
                245                 250                 255

Tyr Thr Phe Pro Leu Ala Glu Lys Val Lys Ala Phe Leu Ala Asp Pro
            260                 265                 270

Ser Ala Phe Val Ala Ala Pro Val Ala Ala Thr Thr Ala Ala
        275                 280                 285

Pro Ala Ala Ala Ala Pro Ala Lys Val Glu Ala Lys Glu Glu Ser
        290                 295                 300

Glu Glu Ser Asp Glu Asp Met Gly Phe Gly Leu Phe Asp
305                 310                 315
```

METHOD AND AGENTS FOR THE DIAGNOSIS AND THERAPY OF CHRONIC INFLAMMATORY INTESTINAL DISEASE

CROSS REFERENCE TO RELATED APPLICATIONS

This application is the National Phase application of International Application No. PCT/EP02/09848, filed Sep. 3, 2002, which designates the United States. This application, in its entirety, is incorporated herein by reference.

The present invention relates to novel methods for diagnosis of inflammatory intestinal diseases, in particular for the diagnosis of the chronically inflammatory intestinal diseases such as Crohn's disease (CD) and Colitis ulcerosa (CU) and their mixed form which is referred to as Colitis indeterminata, which are based on the first evidence of defined antibodies (autoantibodies) in patients suffering from such diseases, and therapeutic methods derivable therefrom and agents which can be used in such therapeutic methods.

The diseases of the gastrointestinal tract include inflammatory intestinal diseases in which the intestinal wall and/or mucous membrane of the intestine are inflamed. Enteritis in the narrower sense is defined as an inflammation of the intestinal wall of the small intestine, while colitis is defined as inflammation of the mucous membrane of the large intestine. Inflammatory intestinal diseases have various causes, for example may be of an infectious nature or may occur as a result of poisoning, and they may occur as acute or chronic diseases. Among the inflammatory intestinal diseases, chronically inflammatory intestinal diseases are of particular importance for the economy and internal medicine owing to their high associated morbidity (disease rate) and mortality (death rate): the diseases known by the names Crohn's disease (synonym: regional enteritis) and Colitis ulcerosa (synonym: Colitis gravis) and their mixed form Colitis indeterminata. Characteristic symptoms are abdominal pain, diarrhoea and, where the small intestine is affected, possibly malabsorption. Intestinal stenoses, internal and external fistulas and abscesses occur in complications in Crohn's disease, whereas severe blood loss and an increased risk of the occurrence of carcinomas of the large intestine (about 40% where the disease has existed over 25 years) occur in the case of Colitis ulcerosa. Clinical characteristics in Crohn's disease are the discontinuous attack of the distal small intestine and of the colon, while a continuous intestinal attack, primarily of the distal sections, is present in the case of Colitis ulcerosa. Histologically, the finding of epithelioid cell granulomas is characteristic of Crohn's disease, and the finding of crypt abscesses is characteristic of Colitis ulcerosa. 5-10% of patients suffering from the chronically inflammatory intestinal diseases show characteristics of both clinical pictures (Colitis indeterminata).

On the basis of knowledge to date, the chronically inflammatory intestinal diseases are multifactorial to a limited extent. The factors discussed include nutritional habits and psychic triggers. A polygenetic predisposition and a number of external influences, particularly from intestinal flora, have been confirmed.

On the basis of the chronic course of the disease and various accompanying phenomena, said chronically inflammatory intestinal diseases have for a relatively long time also been discussed from the point of view of possible autoimmune reactions. However, autoantibodies whose occurrence has the sensitivity (characteristic based on patient; for an optimum specificity of 100%, the antibodies are found in all patients) and specificity (characteristic based on healthy person; for an optimum specificity of 100%, the antibodies are not detectable in any healthy persons) required for diagnostic purposes have however not been characterized to date. The lack of characterization of antibodies closely coupled to the pathological process of the chronically inflammatory intestinal diseases has to date also prevented the character of such diseases from being specifically considered as possible autoimmune diseases in any way in the therapy of said diseases.

The present invention is based on novel discoveries which were made by means of a specially designed analytical method of immunological protein analysis, which is purely empirical and in which, with the exception that a disease manifesting itself in a specific organ or tissue and to be investigated might be an autoimmune disease, no additional hypothetical or theoretical assumptions are made. The analytical method used is explained in more detail below.

The use of the method led to the result that, in patients in whom Crohn's disease or Colitis ulcerosa have been diagnosed on the basis of the clinical findings, antibodies which bind to defined ribosomal proteins which as such have proved to be known, namely the ribosomal proteins P0 and/or L5, are found with high sensitivity and specificity. Their participation in an autoimmune process which takes place in Crohn's disease or Colitis ulcerosa was completely unknown to date.

The experimental findings described herein make it possible for the first time to diagnose said chronically inflammatory intestinal diseases by a corresponding antibody detection in biological samples, in particular in serum, plasma, tissue samples and/or in the stool, with high diagnostic certainty.

The novel discoveries about the nature of the antibodies occurring in said diseases furthermore makes it possible to develop novel therapeutic approaches for the treatment of said diseases which are autoimmune diseases in character.

As a first aspect, the present invention therefore provides a novel diagnostic method, in particular for diagnosis, early diagnosis, differential diagnosis, assessment of the severity and therapy-accompanying monitoring and prognosis, of chronically inflammatory intestinal diseases, in particular Crohn's disease, Colitis ulcerosa and their mixed form Colitis indeterminata, which is characterized in that the presence and/or the amount of one or more antibodies which bind to ribosomal proteins, in particular the ribosomal proteins P0 and L5, are determined in the serum, plasma, tissue samples and/or stool of patients who are suffering from an inflammatory intestinal disease or in whom such a disease is suspected.

The methods for the determination of said antibodies in a biological sample may be any known immunodiagnostic methods which are used for detecting and for measuring antibodies. Preferably, the antibodies are determined with the aid of an immunoassay in which the respective ribosomal protein (P0, L5) in complete form or in the form of an adduct, phosphorylation product, partial peptide or observed splicing variant, in particular of an intestine-specific splicing variant, is used as an antigen for binding the antibodies sought. For marking the antibodies specifically bound from a biological sample, it is then possible to use some suitable anti-human antibody marked in a manner known per se, or a further antigen preparation which contains the antigen used for the antibody binding, or a similar specific antigen, in marked form. Of course, it is preferable if the assay used for the antibody determination ensures the required sensitivity in the range of the antibody concentrations occurring.

The method of determination can also be carried out using chip technology or as a rapid test (point-of-care test). The ribosomal protein P0 and/or L5 to be used as an antigen may be a human or animal protein which was enriched or isolated from suitable natural (human or animal) sources or which has been specifically (recombinantly) produced by a genetic engineering method. Since, for example, the ribosomal protein P0 is found in identical or immunologically very similar form over many species boundaries, a broad range of possibly suitable starting materials from which the required antigen preparations can be obtained is available for the provision of suitable assays.

For the provision of novel possible therapies of the chronically inflammatory intestinal diseases Crohn's disease and *Colitis ulcerosa*, it is possible to follow therapeutic approaches which on the one hand aim at deactivating (blocking) or removing the antibodies involved in the autoimmune process or, on the other hand, at influencing the pathological process in a specific manner by producing immunotolerance. For blocking the antibodies, it is possible to use active substances, for example ribosomes, ribosome fractions, ribosomal proteins or fragments or derivatives thereof which bind and deactivate the circulating antibodies. Such specific binders of said antibodies can also be used for the preparation of materials for affinity purification, by means of which the pathogenic antibodies can be removed extracorporeally by means of a plasmapheresis.

Alternatively, the proteins P0 and/or L5 can be used in complete form or in the form of an adduct, phosphorylation product, partial peptide, peptide analogue or intestine-specific splicing variant as a therapeutic agent for inducing immunotolerance or inducing blocking of the T-cell reactivity in antigen-presenting cells or T-cells by blocking or modulation of the antigen presentation.

The results summarized above were obtained by means of the following, generally applicable analytical procedure:

A purely empirical analytical method which is suitable for establishing an involvement of an autoimmune process in basically any diseases, and which at the same time provides exact information about the binding partners of the autoantibodies occurring in the respective disease, was developed for identifying antibodies (autoantibodies).

The procedure is as follows:

It is assumed that a disease is based on autoimmune reactions or has an autoimmune component, and it is supposed that the autoantibodies characteristic for autoimmune diseases attack tissue structures of those organs or tissues in which the symptoms typical for the respective diseases are particularly pronounced. In order to test the question as to whether typical autoantibodies are involved in the pathological process, an immunoglobulin fraction is then first obtained by unspecific affinity purification from patients who, on the basis of clinical findings, are suffering from the disease to be investigated. At the same time, a corresponding immunoglobulin fraction is obtained from healthy persons. The immunoglobulin fractions obtained from healthy persons and patients are then bound separately to carrier materials for affinity chromatography, so that two columns characterized by different immunoglobulins are obtained for comparative affinity chromatography.

Both columns are then loaded with a tissue extract which can be obtained from healthy tissue but also from a pathological tissue which is attacked in the case of the disease.

If one and the same tissue extract is passed over the two different affinity columns, components which undergo a specific binding reaction with the autoantibodies present on the column are retained from the added tissue extract when additional autoantibodies typical of the disease are bound to the affinity column loaded with patient immunoglobulins.

In the subsequent elution of the columns under conditions in which antigen antibodies bonds are broken, two different eluates (protein fractions) are obtained, the eluate from the affinity column with the patient immunoglobulins optionally containing additional components which were bound to disease-specific autoantibodies present.

If the composition of the eluates is subsequently investigated by 2D gel electrophoresis, the components of the tissue sample which were previously bound by the disease-specific antibodies are detectable as additional spots of the proteins which were not retained by the autoantibody-free affinity column with immunoglobulins of healthy persons.

The protein spots typical of the disease can then be isolated and can be investigated by means of modern methods of protein analysis.

If a tissue fraction from a healthy tissue is used, the additional proteins found are not necessarily the autoantigens which were causatively involved in the origin of the autoimmune reaction. If, for example, the autoimmune reaction is triggered/caused by particular pathological forms of the protein found (e.g. specially processed proteins, organ-specific splicing variants, foreign proteins which, for example, entered the intestine by an infectious route), this need not be reflected in the binding behaviour of the isolated antibodies against the "normal" tissue components used in the test. The exact nature of the pathogenic (triggering) autoantigens is only of secondary importance for the immunodiagnosis, in which all that is important is the reliable assignment of biomarkers to a pathological process. However, in the light of the knowledge about disease-specific occurrence of specific autoantibodies, it is of course also possible in principle, with the use of tissue samples of patients, optionally in combination with autoantibodies of the type found, to determine more exact details of the functional changes which are actually present in the tissues attacked and which are disease-triggering or occur in the patients in interaction with the autoantibodies. Such subsequent discoveries can then optionally be used for further improvement of diagnostic procedures.

In the present case, the inventor's experiments, in which the object was to obtain knowledge about chronically inflammatory intestinal diseases, were carried out using tissue extracts obtained from the small intestine of (healthy) baboons. The tissue extract of primates (baboons) was chosen owing to its easy availability and as experience has shown that there is a very high similarity between the proteins of primates and humans, which manifests itself as high cross-reactivities with many therapeutic and diagnostic human reagents.

By working, as described in more detail below, with the tissue extract from the small intestine of baboons in combination with affinity columns, one of which was loaded with an affinity-purified immunoglobulin fraction of healthy persons while the other had an immunoglobulin fraction of patients suffering from Crohn's disease and/or *Colitis ulcerosa*, it was possible to find, in the eluates from the patient affinity columns, two protein spots which occurred only in the eluates from the affinity columns with the patient immunoglobulins and which, on the basis of gel electrophoresis, have molecular weights of about 36 kD and 38 kD, respectively. The protein spots were isolated from the electrophoresis gel and decomposed by trypsin digestion into fragments which were analyzed in a manner known per se by mass spectrometry and could be identified by comparison with the data for known trypsin-treated proteins.

It emerged that both proteins found were known ribosomal proteins, on the one hand the so-called ribosomal protein P0, which has the known sequence according to SEQ ID NO:2 (database SWISS PROT Entry RLA0_HUMAN 60S acidic ribosomal protein P0; P05388; cf. also N. Fabien et al., (15), Autoantibodies Directed Against the Ribosomal P Proteins are not only Directed Against a Common Epitope of the P0, P1 and P2 Proteins, J. Autoimmun. (1999) 13, 103-110; and the literature cited therein, in particular Wool I. G. et al., Biochimie 73:861-870), and on the other hand the ribosomal protein L5, which has the known sequence according to SEQ ID NO:1 (database SWISS PROT Entry RL5_HUMAN 60S ribosomal protein L5; P46777; cf. also J.-M. Frigerio, J.-C. Dagorn, J. L. Iovanna, (26), Cloning, sequencing and expression of the L5, L21, L27a, L28, S5, S9, S10 and S29 human ribosomal protein mRNAs, Biochim. Biophys. Acta 1262 (1995) 64-68).

It is true that it was known that both proteins or antibodies directed against them play a role in autoimmune diseases, in particular in so-called systemic lupus erythematosus (SLE) (cf. for example J. C. Homberg, M. Rizzetto and Deborah Doniach, (2), Ribosomal Antibodies Detected by Immunofluorescence in Systemic Lupus Erythematosus and other Collagenoses, Clin. Ex. Immunol. (1974) 17, 617-628; Thomas L., (1), Labor und Diagnose [Laboratory and Diagnosis], 5$^{th}$ Edition, 1998, 824-842; A. Giualis et al., (22), Anti-5s RNA/protein (RNP) antibody levels correlate with disease activity in a patient with systemic lupus erythematosus (SLE) nephritis, Clin. Exp. Immunol. 1994, 95, 385-389). Antibodies against the protein P0 are clinically determined in the diagnosis of SLE. An assay developed for this purpose is described in U.S. Pat. No. 4,865,970. A similar enzyme linked immunosorbent assay for the detection and quantitation of antibodies to ribosomal P is furthermore sold as IMMULISA™ Anti-Ribosomal P Kit, ELISA, IMMCO Diagnostics Inc., Buffalo, N.Y. 14228. These assays operate with a relatively short peptide sequence from the carboxy terminus of the protein P0 and the closely related P1 and P2 as specific binders for the antibodies to be determined. Such an assay can also be used in the diagnosis method according to the invention but is less preferable since only some of the relevant antibodies are found using partial peptides of said type (N. Fabien et al., (22), J. Autoimun. (1999) 13, 103-110).

The fact that autoantibodies which bind to said two ribosomal proteins P0 and L5 are also found in patient sera in the case of the chronically inflammatory intestinal diseases Crohn's disease (CD) and *Colitis ulcerosa* (CU) was completely unknown to date.

P0 is a ribosomal protein which is present in identical form or in the form of ribosomal proteins having a very high homology in numerous organisms which range from lower organisms, e.g. parasites, to humans. It is known that it occurs in pentamer complexes in the large subunit of ribosomes. Extensive scientific literature exists on the ribosomal protein P0, to which literature reference is hereby made generally by reference to the examples in the attached list of references, in particular numbers 1-16. In view of the finding in the present Application, it is of particular interest that P0 is overexpressed (7, 8) in the case of intestinal carcinomas and carcinomas of the liver, and, depending on the tissues, is also expressed on the surface of cell membranes (5), which is of interest with regard to the intestinal specificity of CD and CU. It should furthermore be mentioned that antibodies against ribosomal P proteins, to which P0 belongs, are also discussed from the point of view of anti-lymphocyte antibodies (3, 4).

There is also extensive scientific literature on the ribosomal protein L5. In this context, reference is once again made generally to the examples in the list of references, in particular numbers 18-27. In connection with the findings in the present Application, it is of particular interest that L5 interacts with numerous proteins, for example those having an enzyme function (e.g. protein phosphatase-1 (19) or calmodulin kinase-2 (27)), and that L5 furthermore occurs in complexes with RNA (19-23) and in this complexed form can act as an antigen. It is moreover to be expected that the findings in the present Application will give strong new impetus to research.

The discovery and identification of the proteins which bonded only to antibodies detectable in the CD or CU patients are described in more details below, reference being made to the attached sequence listings.

The figures show the following:

FIG. 1 shows view of 2D electrophoresis gels which permit a comparison of the spot patterns of the eluates of an affinity column containing immunoglobulins from sera of healthy persons (A) with those of an affinity column containing the immunoglobulins from sera of CD or CU patients (B). The bordered region shows the position of the first protein which can be eluted only from the patient affinity columns;

FIG. 2 shows views of 2D electrophoresis gels which permit a comparison of the spot patterns of the eluates of an affinity column containing immunoglobulins from sera of healthy persons (A) with those of an affinity column containing the immunoglobulins from sera of CD or CU patients (B). The bordered region shows the position of the second protein which can be eluted only from patient affinity columns;

Figure 2B:
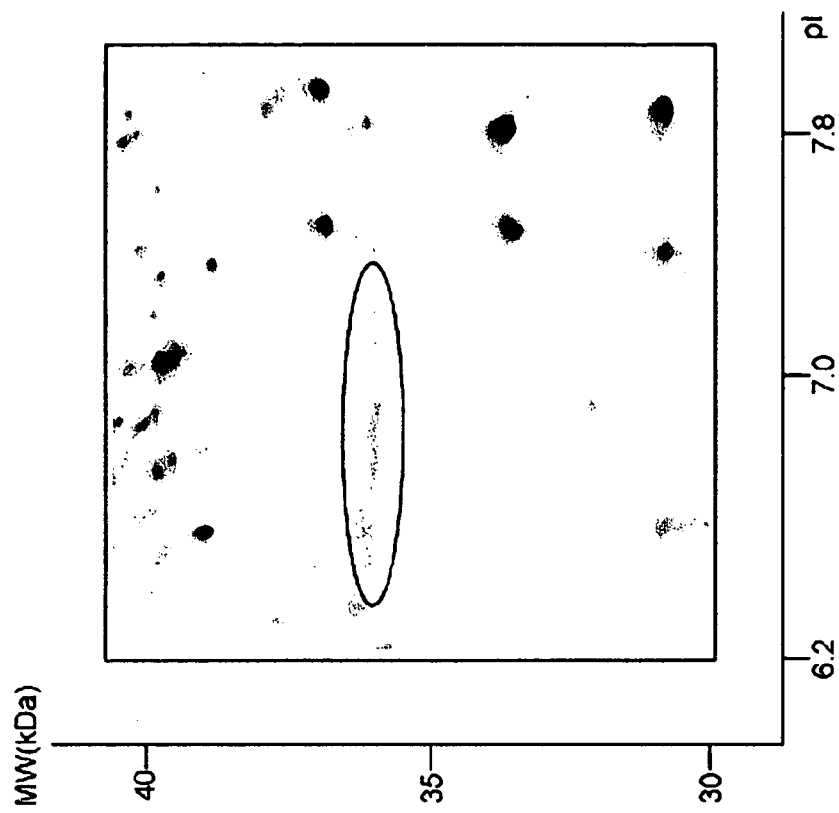

1. Preparation of an Extract from the Small Intestine of Baboons

Adult baboons (2-3 years old, 25-35 kg, male and female) were sacrificed by means of intravenous administration of dolethal (10 ml). The small intestine was removed within 15 min, washed with water, divided into approx. 10 g pieces and immediately frozen in liquid nitrogen.

In the further processing, samples of the individual deep-frozen small intestine tissues were pulverized in a porcelain mortar to give a powder while cooling with nitrogen (cf. J. Klose, "Fractionated Extraction of Total Tissue Proteins from Mouse and Human for 2-D Electrophoresis", in: Methods in Molecular Biology, Vol. 112, 2-D Proteome Analysis Protocols, Humana Press Inc., Totowa, N.J.). All further steps were carried out at +4° C. The powder was taken up in 100 ml of buffer (50 mM Hepes, 50 mM NaCl, pH 8) and homogenized by means of a 60 ml potter (from Braun Melsungen) in 5 up-and-down movements at 900 rpm. After subsequent centrifuging for 1 hour at 100,000 g, the supernatant obtained (tissue extract) was recovered and was used for the further investigations.

2. Preparation of Immunoglobulin Preparations and Affinity Columns

The immunoglobulins were isolated from sera of patients with Crohn's disease or *Colitis ulcerosa* on the one hand and from healthy persons on the other hand (control sera) by means of an unspecific affinity purification via protein G agarose. For this purpose, in each case 0.2 ml of serum was mixed with 0.2 ml of PBS and then 0.5 ml of protein G agarose (packed gel) was added. The mixture is incubated for 30 min with gentle shaking and then introduced into a glass column (diameter 0.5 cm) which was closed at the lower end with a fine frit. The column is first washed with PBS (5 ml), and bound immunoglobulins are then eluted with 20 mM citric acid (pH approx. 2.5) (flow rate approx. 1 ml/min). The immunoglobulin eluate is neutralized by adding TRIS-HCl, 1 M, pH 8.0.

The purified immunoglobulin fraction is then oxidized for 20 min with addition of sodium periodate (final concentration 10 mg/ml). The sodium periodate is then removed by desalination by means of an NAP-5 column (Pharmacia) according to the manufacturer's method, PBS being used in the column and as elution buffer.

The desalinated oxidized immunoglobulin fraction is mixed with Carbolink material (0.5 ml of packed gel, washed with PBS, from Pierce). After incubation for 12 h with gentle shaking, the affinity material obtained and coated with the respective immunoglobulin fractions is introduced into a glass column (diameter 0.5 cm) having a fine frit and is washed with 10 ml of PBS.

3. Working Up the Intestinal Extract by Affinity Purification

In each case 5 ml of a baboon intestinal extract according to 1. are added continuously and repeatedly at a flow rate of 0.5 ml/min for one hour over in each case an affinity column loaded with an immunoglobulin fraction according to 2. The columns are then washed with 5 ml of PBS. The outflow is continuously monitored for absorption at 280 nm.

The proteins bound to the affinity columns are then eluted with 20 mM citric acid (pH approx. 2.5). The eluates obtained are then analyzed by means of 2-D gel electrophoresis.

4. Proteome Analysis Using the Eluates of the Affinity Columns

In the initial analytical 2D gel electrophoresis, the individual eluates were separated by means of analytical 2D gel electrophoresis, as described in J. Klose et al., "Two-dimensional electrophoresis of proteins: An updated protocol and implications for a functional analysis of the genome", Electrophoresis 1995, 16, 1034-1059. The visualization of the protein in the 2D electrophoresis gel was effected by means of silver staining (cf. J. Heukeshoven et al., "Improved silver staining procedure for fast staining in Phast-System Development Unit. I. Staining of Sodium dodecyl gels", Electrophoresis 1988, 9, 28-32). The stained gels were dried using a Biorad 583 gel dryer.

Figure 2A:
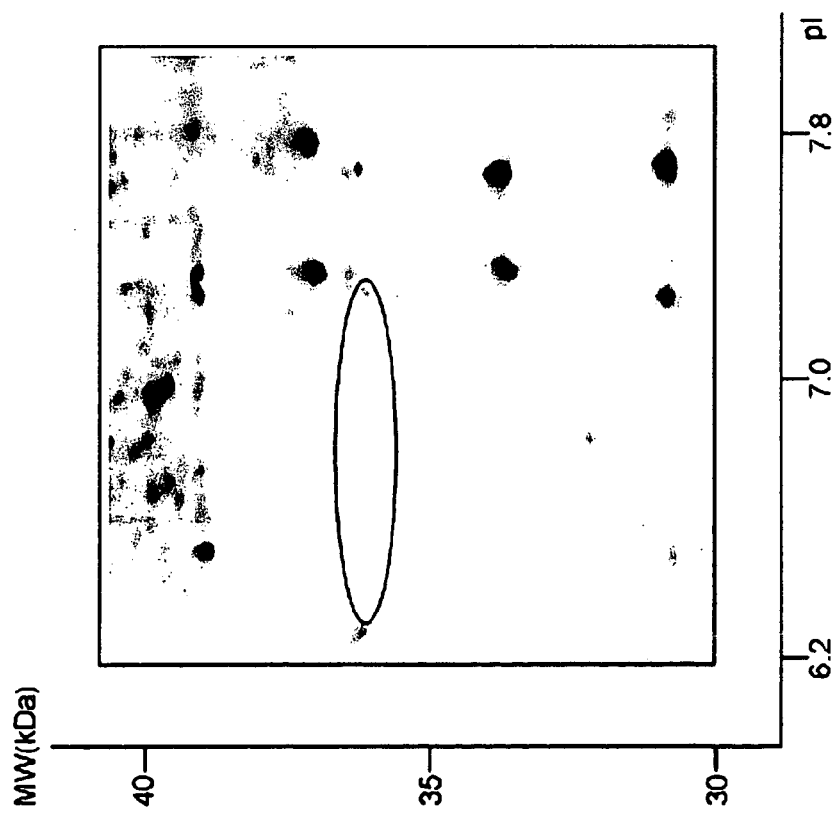

For evaluation, the protein spot pattern of an eluate from the affinity column containing the immunoglobulins of healthy persons was compared with the protein spot pattern which resulted from a corresponding eluate from the affinity column containing immunoglobulins of CD or CU patients. Protein spots which never occurred in healthy persons but were always additionally present in the case of patient samples were selected for further analytical investigations. FIG. 1 and FIG. 2 show pictures of 2D electrophoresis gels which permit the comparison of the spot patterns of the eluates of an affinity column containing immunoglobulins from sera of healthy persons (A) with those of an affinity column containing the immunoglobulins from sera of CD or CU patients (B). The bordered regions show the positions of the proteins which can be eluted only from the patient affinity columns.

Surprisingly, two novel protein spots or protein bands were found in the eluates from the patient column: one spot at a molecular weight of about 38 kD and a pI of about 5.5 and a sharp band at the molecular weight of about 36 kD, which, however, appeared as an elongated strip-like spot in the pI direction. The two novel protein spots occurred in all eluates from patient columns but were not visible in the eluates from the columns containing immunoglobulins of healthy persons.

The novel specific proteins identified in the protein spot pattern of the analytical 2D gel electrophoresis were then prepared by means of preparative 2D gel electrophoresis (cf. Klose, loc cit). The staining was effected by means of Coomassie Brilliant Blue G250 (cf. V. Neuhoff et al., Electrophoresis 1988, 9, 255-262; and Electrophoresis 1990, 11, 101-117).

Figure 3:
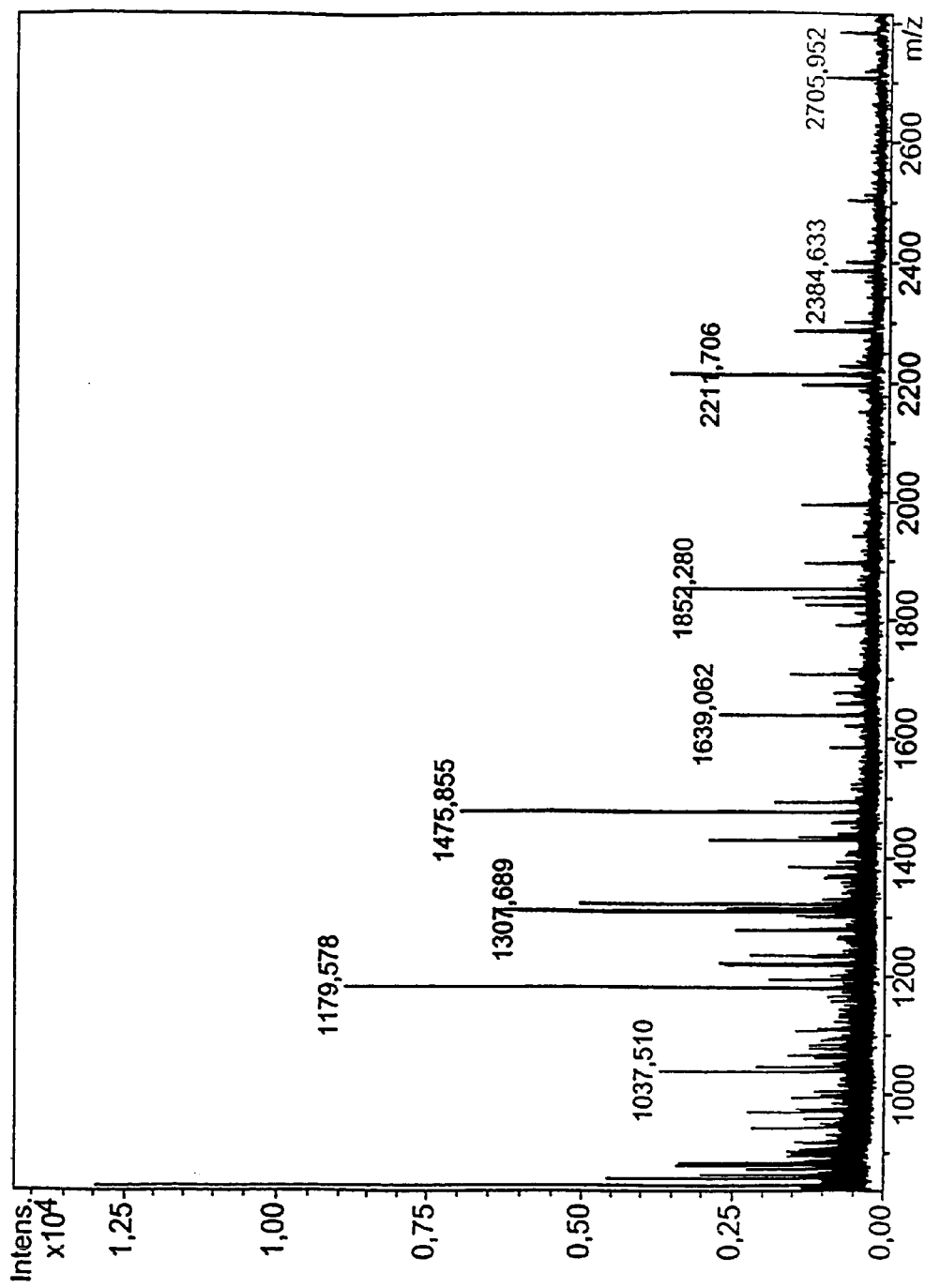
FIG. 3 shows the mass spectrum of the trypsin-digested product isolated from the gel of the 2D electrophoresis according to FIG. 1 (B)
Figure 4:
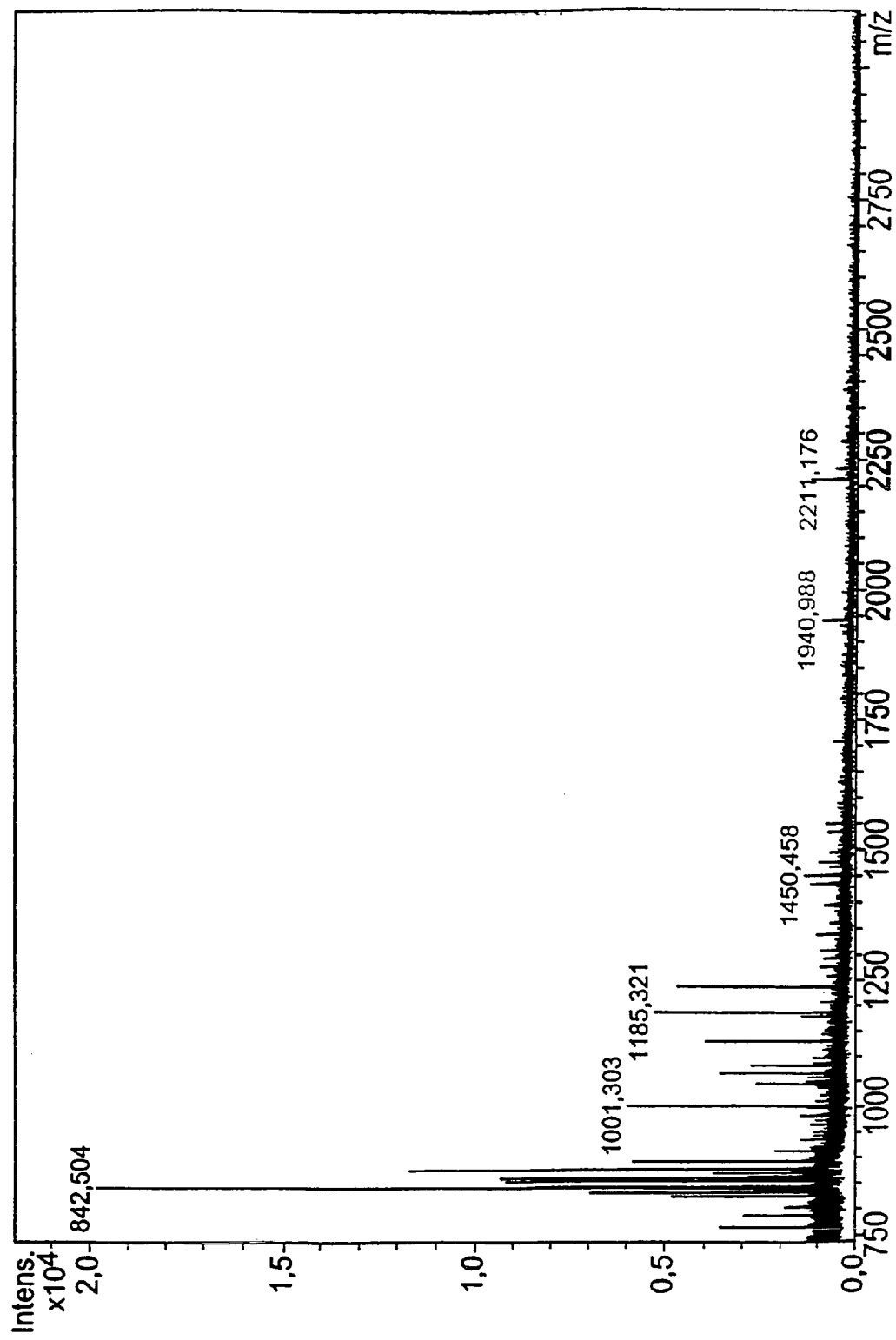
FIG. 4 shows the mass spectrum of the trypsin-digested product isolated from the gel of the 2D gel electrophoresis according to FIG. 2 (B).

The protein spots preselected for the further analysis were cut out of the gel, using the method described in Courchesne PL et al., In: Methods in Molecular Biology, Vol. 112:487-513, trypsin-digested and analyzed by mass spectroscopy using mass spectrometric investigations as likewise described and discussed in Courchesne PL, loc cit. The fragment patterns (FIGS. 3 and 4) obtained in the mass spectroscopy (MALDI-MS) of the two novel spots were then compared with fragment patterns of known proteins available from the databases. Various Internet software programs were used for this purpose. First, the peptide masses determined by MALDI-MS were matched with the theoretical peptide masses of all known mammalian proteins. For the protein search (in the Owl.7.2.2001 database using the search program Protein Prospector), monoisotopic masses with mass tolerances of 100 ppm (P0) or 200 pm (L5) were permitted. The further search was carried out with the NCBinr. database using the search program ProFound in the case of the protein from FIG. 1B (P0), and with the database NCBI (2001/07/20) using the search program ProFound (species: *Mammalia*) and a mass tolerance of 200 ppm in the case of the protein from FIG. 2B.

The two proteins typical of the disease were unambiguously identified as the ribosomal proteins P0 having the amino acid sequence according to SEQ ID NO:1 and L5 having the amino acid sequence SEQ ID NO:2, said proteins being known per se.

5. Qualitative Comparison Between Controls and Pathological Samples

The results shown in the following table were obtained by preparing individual affinity columns according to the above procedure, using in each case 10 sera of healthy persons (control), 10 sera of CD patients and 10 sera of CU patients, and treating said columns with the above-mentioned intestinal extract.

TABLE

| Sample | P0 | L5 |
|---|---|---|
| Control 1 | − | − |
| Control 2 | − | − |
| Control 3 | − | − |
| Control 4 | − | − |
| Control 5 | − | − |
| Control 6 | − | − |
| Control 7 | − | − |
| Control 8 | − | − |
| Control 9 | − | − |
| Control 10 | − | − |
| CD patient 1 | + | + |
| CD patient 2 | + | + |
| CD patient 3 | + | + |
| CD patient 4 | + | + |
| CD patient 5 | + | + |

TABLE-continued

| Sample | P0 | L5 |
|---|---|---|
| CD patient 6 | − | + |
| CD patient 7 | + | + |
| CD patient 8 | + | − |
| CD patient 9 | + | + |
| CD patient 10 | + | + |
| CU patient 1 | + | + |
| CU patient 2 | − | + |
| CU patient 3 | + | + |
| CU patient 4 | + | + |
| CU patient 5 | − | + |
| CU patient 6 | + | + |
| CU patient 7 | + | + |
| CU patient 8 | + | * |
| CU patient 9 | + | − |
| CU patient 10 | + | + |

It is evident from the table that both types of antibodies are to be found simultaneously in most CD and CU patients, but at least one type of antibody is to be found in all CD or CU patients. On the other hand, such antibodies are not found in any serum of the healthy control persons. In the relatively limited group of test persons investigated, the selectivity was thus 100%. When both antibodies were determined and the evidence of an antibody type appeared to be diagnostically significant, the sensitivity was also 100%.

LIST OF REFERENCES

1. Thomas L., Labor und Diagnose, 5th Edition, 1998, 824-842.
2. J.-C. Homberg, M. Rizzetto and Deborah Doniach, Ribosomal Antibodies Detected by Immunofluorescence in Systemic Erythematosus and other Collagenosis, Clin. exp. Immunol. (1974) 17, 617-628.
3. J. B. Winfield, Are anti-ribosomal P protein antibodies a type of anti-lymphocyte antibody? Clin. Exp. Immunol. 1997, 109, 1-3.
4. Stafford H A, Chen A E, Anderson C J et al., Anti-ribosomal and 'P-peptide'-specific autoantibodies bind to T lymphocytes, Clin. Exp. Immunol. 1997; 109, 12-19.
5. H.-H. Sun, W.-T. Liu, S.-Y. Tang, C.-Y. Tsai, S.-C. Hsieh, T.-H. Wu, S.-H. Han, The expression of acidic ribosomal phosphoproteins on the surface membrane of different tissues in autoimmune and normal mice which are the target molecules for anti-double-stranded DNA antibodies, Immunology 1996, 87, 362-371.
6. David T. Grabowski, Walter A. Deutsch, Dennis Derda and Mark R. Kelley, Drosophila AP3, a presumptive DNA repair protein, is homologous to human ribosomal associated protein P0, Nucleic Acids Research, Vol. 19, 4297, 1991
7. Nobuo Kondoh, Toru Wakatsuki, Akihide Ryo, Akiyuki Hada, Tsukasa Aihara, Sankichi Horiuchi, Narihide Goseki, Osamu Matsubara, Kenji Takenaka, Mizue Shichita, Kenji Tanaka, Masahiro Shuda and Mikio Yamamoto, Identification and Characterization of Genes Associated with Human Hepatocellular Carcinogenesis, Cancer Res. 59, 4990-4996, 1999
8. M. A. Rodrigues-Gabriel, M. Remacha and J. P. G. Ballesta, Phosphorylation of Ribosomal Protein P0 Is Not Essential for Ribosome Function but Can Affect Translation, Biochemistry 1998, 37, 16620-16626
9. G. F. Barnard, R. J. Staniunas, Shideng Bao, Kenichi Mafune, G. D. Steele Jr., J. L. Gollan and Lan Bo Chen, Increased Expression of Human Ribosomal Phosphoprotein P0 Messenger RNA in Hepatocellular Carcinoma and Colon Carcinoma, Cancer Res. 52, 3067-3072, 1992
10. K.-H. Sun, W.-T. Liu, C.-Y. Tsai, S.-J. Tang, S.-H. Han, C.-L. Yu, Anti-dsDNA antibodies cross-react with ribosomal P proteins expressed on the surface of glomerular mesangial cells to exert a cytostatic effect, Immunology 1995, 85, 262-269
11. I. Ferrari, M. J. Levin, G. Wallukat, R. Elies, D. Lebesgue, P. Chiale, M. Elizari, M. Rosenbaum and J. Hoebeke, Molecular Mimicry between the Immunodominant Ribosomal Protein P0 of Trypanosoma cruzi and a Functional Epitope on the Human $\beta_1$-Adrenergic Receptor, J. Exp. Med., Vol. 182, 1995, 59-65
12. S. Chatterjee, S. Singh, R.Sohoni, V. Kattige, Ch. Deshpande, Sh. Chiplunkar, N. Kumar, Sh. Sharma, Characterization of domains of the phosphoriboprotein P0 of Plasmodium falciparum, Mol. Biochem. Parasitol. 107 (2000) 143-154
13. S. Chatterjee, S. Singh, R. Sohoni, N. J. Singh, A. Vaidya, C. Long and Sh. Sharma, Antibodies against Ribosomal Phosphoprotein P0 of Plasmodium falciparum Protect Mice against Challenge with Plasmodium yoelli, Infect. Immun. Vol. 68, 2000, 4312-4318
14. A. Goswami, S. Singh, V. D. Redkar and Sh. Sharma, Characterization of P0, a Ribosomal Phosphoprotein of Plasmodium falciparum, J. Biol. Chem. Vol. 272, 12138-12143, 1997
15. N. Fabien et al., Autoantibodies Directed Against the Ribosomal P Proteins are not only Directed Against a Common Epitope of the P0, P1 and P2 Proteins, J. Autoimmun. (1999), 13, 103-110
16. B. Liliensiek et al., identification of Four Genes in Endothelial Cells Whose Expression is Affected by Tumor Cells and Host Immune Status—A Study in Ex Vivo-Isolated Endothelial Cells, Blood, Vol. 92 (9), 1998, 3394-3404
17. R. Szyszka, G. Bou, J. P. G. Ballesta, RAP Kinase, a new enzyme phosphorylating the acidic P proteins from Sacharomyces cerevisiae, Biochim. Biophys. Acta 1293, (1996), 213-221
18. O. Rosorius et al., Human Ribosomal Protein L5 Contains Defined Nuclear Localization and Export Signals, J. Biol. Chem., Vol. 275, 12061-12068, 2000
19. K. Hirano et al., Interaction of the Ribosomal Protein, L5, with Protein Phosphatase Type 1, J. Biol. Chem. Vol. 270, 19786-19790, 1995
20. W. M. Michael and G. Dreyfuss, Distinct Domains in Ribosomal Protein L5 Mediate 5 S rRNA Binding and Nuclear Localization, J. Biol. Chem. Vol. 271, 11571-11574, 1996
21. M. Claußen, F. Rudt and T. Pieler, Functional Modules in Ribosomal Protein L5 for Ribonucleoprotein Complex Formation and Nucelocytoplasmic Transport, J. Biol. Chem. Vol. 274, 33951-33958, 1999
22. A Giualis et al., Anti-5S RNA/protein (RNP) antibody levels correlate with disease activity in a patient with systemic lupus erythematosus (SLE) nephritis, Clin. Exp. Immunol. 1994, 95, 385-389
23. V. Marechal et al., The Ribosomal L5 Protein Is Associated with mdm-2 and mdm-2-p53 Complexes, Mol. Cell. Biol. Vol. 14, 7414-7420, 1994

24. O. Spirina et al., Heart-specific splice-variant of a human mitochondrial ribosomal protein (mRNA processing; tissue specific splicing), Gene 261 (2000) 229-234
25. J.-M. Kim et al., Interaction of the β Subunit of Casein Kinase II with the Ribosomal Protein L5, BBRC 226, 180-186 (1996)
26. J.-M. Frigerio, J.-C. Dagorn, J. L. Iovanna, Cloning, sequencing and expression of the L5, L21, L27a, L28, S5, S9, S10 and S29 human ribosomal protein mRNAs, Biochim. Biophys. Acta 1262 (1995) 64-68
27. B. Gueraa, O.-G. Issinger, p53 and the ribosomal protein L5 participate in high molecular mass complex formation with protein kinase CK2 in murine teratocarcinoma cell line F9 after serum stimulation and cisplatin treatment, FEBS Letters 434 (1998) 115-120

The invention claimed is:

1. A method for diagnosis of chronic inflammatory intestinal diseases, wherein the method comprises contacting a biological sample from a patient in whom chronic inflammatory intestinal disease is suspected with a molecule that detects an autoantibody directed to a ribosomal protein selected from P0 and L5, wherein the presence of said autoantibody indicates chronic inflammatory intestinal disease.

2. The method according to claim 1, wherein the chronic inflammatory intestinal disease is selected from Crohn's disease and *Colitis ulcerosa* or their mixed form designated as *Colitis indeterminate*.

3. The method according to claim 2, wherein said autoantibody is determined with the aid of an immunoassay in which the respective ribosomal protein in complete form or in the form of an adduct, or a phosphorylation product, is used as an antigen for binding and/or detecting the antibodies to be determined.

4. The method according to claim 1, wherein said autoantibody is determined with the aid of an immunoassay in which the respective ribosomal protein in complete form or in the form of an adduct, or a phosphorylation product is used as an antigen for binding and/or detecting autoantibodies.

5. The method according to claim 4, wherein the ribosomal protein is a human or animal protein which is enriched or isolated from natural sources or is recombinantly produced by a genetic engineering method.

* * * * *